(12) United States Patent
Kawamura et al.

(10) Patent No.: US 9,533,931 B2
(45) Date of Patent: Jan. 3, 2017

(54) PROCESS OF PRODUCING 1,4-BUTANEDIOL

(71) Applicant: Toray Industries, Inc., Tokyo (JP)

(72) Inventors: Kenji Kawamura, Kamakura (JP); Izumi Morita, Tokai (JP); Masateru Ito, Kamakura (JP); Satoshi Sakami, Kamakura (JP); Masataka Makino, Nagoya (JP); Katsushige Yamada, Kamakura (JP); Mark J. Burk, San Diego, CA (US); Michael Japs, San Diego, CA (US); Warren Clark, San Diego, CA (US)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/783,894

(22) PCT Filed: Apr. 9, 2014

(86) PCT No.: PCT/IB2014/001279
§ 371 (c)(1),
(2) Date: Oct. 12, 2015

(87) PCT Pub. No.: WO2014/170759
PCT Pub. Date: Oct. 23, 2014

(65) Prior Publication Data
US 2016/0052845 A1    Feb. 25, 2016

Related U.S. Application Data

(60) Provisional application No. 61/811,223, filed on Apr. 12, 2013.

(30) Foreign Application Priority Data

Apr. 17, 2013    (JP) ................. 2013-086802

(51) Int. Cl.
| C08G 63/02 | (2006.01) |
| C07C 29/80 | (2006.01) |
| C07C 67/08 | (2006.01) |
| C08G 63/183 | (2006.01) |
| B01D 3/14 | (2006.01) |
| B01D 3/34 | (2006.01) |
| B01D 15/36 | (2006.01) |
| B01D 61/02 | (2006.01) |

(52) U.S. Cl.
CPC .............. *C07C 29/80* (2013.01); *B01D 3/143* (2013.01); *B01D 3/145* (2013.01); *B01D 3/34* (2013.01); *B01D 15/361* (2013.01); *B01D 61/025* (2013.01); *C07C 67/08* (2013.01); *C08G 63/183* (2013.01); *B01D 2311/2623* (2013.01); *B01D 2311/2669* (2013.01)

(58) Field of Classification Search
CPC .................................................. C07C 29/80
USPC ...................................... 528/308.8; 435/158
See application file for complete search history.

(56) References Cited

U.S. PATENT DOCUMENTS

| 4,154,970 A | 5/1979 | Beer et al. |
| 6,361,983 B1 | 3/2002 | Ames |
| 6,387,224 B1 | 5/2002 | Pinkos et al. |
| 2009/0047719 A1 | 2/2009 | Burgard et al. |
| 2015/0087038 A1* | 3/2015 | Utsunomiya ........... C07C 29/80 435/158 |

FOREIGN PATENT DOCUMENTS

| JP | 05-038291 A | 2/1993 |
| JP | 11-196888 A | 7/1999 |
| JP | 2007-197654 A | 8/2007 |
| JP | 2010-150248 A | 7/2010 |
| JP | 2013-032350 A | 2/2013 |
| WO | 2004/099110 A1 | 11/2004 |
| WO | 2008/115840 A2 | 9/2008 |
| WO | 2010/030711 A2 | 3/2010 |
| WO | 2010/141780 A1 | 12/2010 |
| WO | 2010/141920 A2 | 12/2010 |

OTHER PUBLICATIONS

Karen M. Draths et al., "Environmentally compatible synthesis of adipic acid from D-glucose," J. Am. Chem. Soc., 1994, vol. 116, No. 1, pp. 399-400 (p. 399).

* cited by examiner

*Primary Examiner* — Terressa Boykin
(74) *Attorney, Agent, or Firm* — DLA Piper LLP (US)

(57) ABSTRACT

A process produces 1,4-butanediol by purifying 1,4-butanediol originated from a fermentation broth, by which process 1,4-butanediol having properties suited as a material of producing a polyester is obtained, which 1,4-butanediol enables to reduce by-production of tetrahydrofuran during the esterification reaction and to reduce the delay in polymerization. The process of producing 1,4-butanediol includes adding an alkaline substance other than an ammonia or an amine to an aqueous 1,4-butanediol-containing solution originated from a fermentation broth; distilling the resulting mixture; and recovering a 1,4-butanediol-containing solution from the vapor flow.

15 Claims, 1 Drawing Sheet

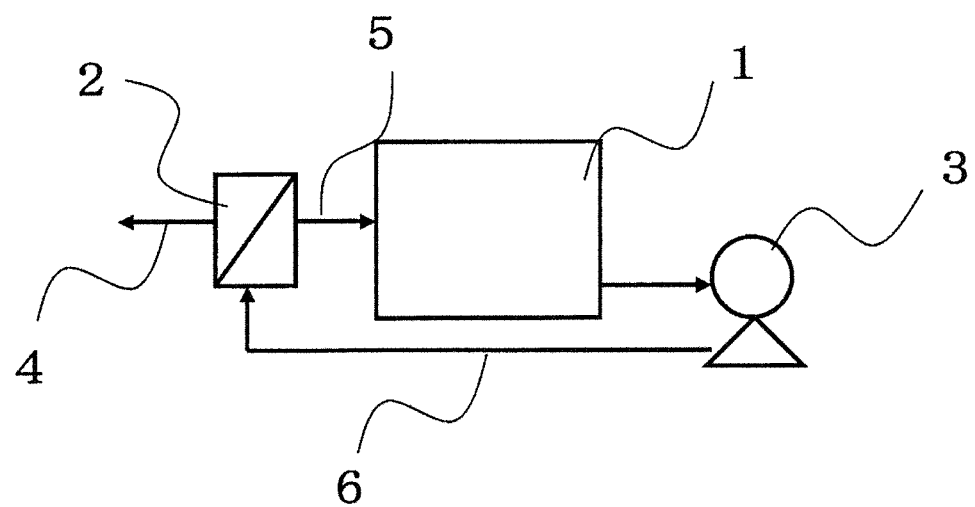

PROCESS OF PRODUCING 1,4-BUTANEDIOL

TECHNICAL FIELD

This disclosure relates to a process of producing 1,4-butanediol originated from a fermentation broth, which is suitable as a material of polyesters.

BACKGROUND

Polyesters obtained by a polycondensation reaction between a diol and a dicarboxylic acid are widely used in various uses such as fibers, films and bottles because of their excellent properties. 1,4-butanediol (hereinafter also referred to as "1,4-BDO") is used as a material to produce polybutylene terephthalate (hereinafter also referred to as "PBT") by polymerization with terephthalic acid, and as a material to produce polybutylene succinate (hereinafter also referred to as "PBS") by polymerization with succinic acid. Since PBT has excellent moldability, heat resistance, mechanical properties and chemical resistance, polyesters are widely used not only as materials for molding electric parts and automobile parts, but also as fibers having a soft texture and stretch properties. Further, PBS is also expected as a biodegradable material attaining biodegradation of used molded articles and attaining composting.

Known industrial methods of producing 1,4-butanediol which is a constituent component of PBT and PBS include a method wherein acetylene and formaldehyde are reacted and then the reaction product is hydrogenated; and a method wherein butadiene is reacted with acetic acid in the presence of palladium catalyst to yield a 1,4-diacetoxy product, and the product is then subjected to reduction and hydrolysis. Further, in recent years, due to the concern about the rise of the price or depletion of petroleum, methods of producing a monomer originated from a biomass resource are attracting attention. Known methods of producing 1,4-butanediol originated from a biomass resource include a method wherein 1,4-butanediol is directly obtained by fermentation; and a method wherein succinic acid obtained by a fermentation method is reduced by hydrogenation to indirectly obtain 1,4-butanediol.

As a purification method of 1,4-butanediol, distillation is known. However, the problems per se of the by-production of THF during the production of polyesters, and of the extension of polymerization time were not reported. U.S. Pat. No. 4,154,970 B discloses a method wherein butanediol generated by ester exchange in the polymerization of PBT is distilled after adding thereto a base such as alkaline metal alcoholate; and U.S. Pat. No. 6,387,224 B discloses a method wherein the 1,4-butanediol mixture obtained by hydrogenation of a maleic acid derivative is distilled after adding an alkaline substance to obtain 1,4-butanediol with small contents of specific impurities. However, the 1,4-butanediol described in those publications is not originated from microbial fermentation, and they are silent about the problems of by-production of THF during production of polyester and of the extension of polymerization time. JP 2013-32350 A discloses a method of obtaining purified 1,4-butanediol having decreased impurities wherein a crude 1,4-butanediol originated from a fermentation broth, which contains as an impurity 2-(hydroxybuthoxy)-tetrahydrofuran, is heated in the presence of an amine. However, JP '350 is silent about 1) an alkaline substance other than an amine and 2) extension of the polymerization time during production of the polyester when the 1,4-butanediol originated from a fermentation broth is used. Further, JP 2010-150248 A discloses a method wherein a 1,4-butanediol-containing solution (not an actual fermentation broth) is treated with a nanofiltration membrane to remove impurities such as inorganic salts, saccharides and proteins to improve the distillation yield. However, those publications are silent about the problems of by-production of THF during the production of polyester and of the extension of polymerization time. WO 2010/141780 A discloses, among other things, methods of purifying 1,4-butanediol.

We discovered problems in using 1,4-butanediol originated from microbial fermentation from which the removal of the impurities is insufficient as a material to produce a polyester, which problems are that THF is by-produced, and the polymerization time is greatly extended when compared to 1,4-butanediol originated from petroleum.

Accordingly, it could be helpful to provide a process of producing 1,4-butanediol suited for a material of producing polyesters, by which process by-production of THF during the esterification reaction of 1,4-butanediol is reduced and the extension of polymerization time is reduced even though the 1,4-butanediol originates from a fermentation broth.

SUMMARY

We discovered that by adding an alkaline substance when 1,4-butanediol originated from a fermentation broth is distilled, by-production of THF during the esterification reaction of 1,4-butanediol is reduced and the extension of polymerization time is reduced so that a 1,4-butanediol suited as a material of producing polyesters is obtained.

We thus provide the following (1) to (7):
(1) A process of producing 1,4-butanediol, comprising the steps of (a) adding an alkaline substance other than an ammonia or an amine to an aqueous 1,4-butanediol-containing solution originated from a fermentation broth; (b) distilling the resulting mixture of step (a); and (c) recovering a 1,4-butanediol-containing solution from the vapor flow.
(2) The process according to (1), wherein the alkaline substance is added in an amount of not more than 20 mol % based on the 1,4-butanediol.
(3) The process according to (1) or (2), wherein the alkaline substance is at least one selected from the group consisting of alkaline metal hydroxides, alkaline metal salts, alkaline earth metal hydroxides and alkaline earth metal salts.
(4) The process according to any one of (1) to (3), wherein the alkaline substance is at least one selected from the group consisting of sodium hydroxide, potassium hydroxide, calcium hydroxide, magnesium hydroxide, sodium carbonate and calcium carbonate.
(5) The process according to any one of (1) to (4), wherein, before adding the alkaline substance, the aqueous 1,4-butanediol-containing solution originated from a fermentation broth is subjected to a step of filtering the aqueous 1,4-butanediol-containing solution through a nanofiltration membrane and recovering the aqueous 1,4-butanediol-containing solution from the permeate flow of the membrane; and/or a step of subjecting the aqueous 1,4-butanediol-containing solution to an ion exchange treatment.
(6) The process according to any one of (1) to (5), wherein, before adding the alkaline substance, said aqueous 1,4-butanediol-containing solution originated from a fermentation broth is subjected to a step of filtering the aqueous 1,4-butanediol-containing solution through a reverse osmosis membrane to increase the concentration of 1,4-butanediol.

(7) A process of producing a polyester, comprising reacting the 1,4-butanediol obtained by the process according to any one of (1) to (6) with a dicarboxylic acid.

(8) The process of producing a polyester according to (7), wherein the dicarboxylic acid is terephthalic acid.

1,4-butanediol having a high purity and no color which is suited as a material of polyesters can be produced, and by using the 1,4-butanediol, by-production of THF and extension of polymerization time in the production of polyesters can be reduced.

BRIEF DESCRIPTION OF THE DRAWINGS

FIG. 1 is a schematic view showing one example of a membrane separation apparatus used in the Examples.

DETAILED DESCRIPTION

The aqueous 1,4-butanediol-containing solution originates from a fermentation broth. As long as the solution originates from a fermentation broth, the solution may be one directly obtained by cultivation of a microorganism together with an assimilable biomass resource, which microorganism is capable of assimilating the biomass resource; or the solution may be obtained by converting an intermediate such as succinic acid obtained by cultivation of a microorganism together with an assimilable biomass resource which microorganism is capable of assimilating the biomass resource, to 1,4-butanediol by a chemical reaction. As long as the aqueous 1,4-butanediol-containing solution originates from a fermentation broth, the solution may be a fermentation broth per se, or one obtained after one or more steps from the fermentation broth, or one obtained after one or more chemical reactions.

Examples of known methods of directly obtaining 1,4-butanediol by fermentation of a microorganism together with an assimilable biomass resource which microorganism is capable of assimilating the biomass resource include the methods of producing 1,4-butanediol described in WO 2008/115840, WO 2010/030711 and WO 2010/141920, respectively, the subject matter of which is incorporated herein by reference.

Examples of the method of converting an intermediate originated from a microbial fermentation of a biomass resource include the methods of converting an intermediate obtained by a cultivation of a known microorganism to 1,4-butanediol by one or more chemical reactions, wherein the intermediate is, for example, succinic acid, succinic anhydride, a succinic acid ester, maleic acid, maleic anhydride, a maleic acid ester, tetrahydrofuran, γ-butyrolactone or the like. Among those methods, a method wherein succinic acid is reduced by hydrogenation in the presence of a reduction catalyst to obtain 1,4-butanediol is efficient and preferred (e.g., the method described in JP 4380654 B).

Examples of the carbon source in the fermentation material include saccharides such as glucose, fructose, sucrose, xylose, arabinose, galactose, mannose and starch. These saccharides may be those commercially available, or may be decomposition products of biomass such as recycled materials and trees and plants, and the decomposition products obtained by a chemical or biological treatment of a cellulose-, hemicellulose- or lignin-containing material can be used. In these cases, it is preferred that the impurities which inhibit the fermentative production have been decreased.

Examples of the nitrogen source in the fermentation material include inorganic nitrogen sources such as ammonia gas, aqueous ammonia, ammonium salts, urea and nitrates; and organic nitrogen sources such as oil cake, soybean hydrolysate, casein hydrolysate, meat extract, yeast extract, peptone, amino acids and vitamins.

Examples of the inorganic salts used as a fermentation material include phosphoric acid salts, magnesium salts, calcium salts, manganese salts and the like, and these inorganic salts may be added as desired. When the microorganism used for fermentation needs a specific nutrient (such as an amino acid) for the growth thereof, the nutrient itself or a natural material containing the nutrient is added. An anti-foaming agent may also be used as desired.

As for the cultivation conditions when 1,4-butanediol is directly produced by fermentation, conditions for the microorganism can be selected, and the cultivation can be carried out by the method described in, for example, WO 2010/141920 and US 2009-0047719 A, filed on Aug. 10, 2007, the subject matter of which is incorporated herein by reference. The fermentation may be carried out by a batch process, continuous process or a fed-batch process as described in that U.S. publication.

If desired, a base such as sodium hydroxide, or an acid may be added to keep the pH of the culture medium at a desired pH such as a neutral pH in the vicinity of 7. The rate of glucose-intake can be measured by monitoring the consumption of carbon source with time by measuring the optical density with a spectrophotometer (600 nm) to measure the growth rate of the microorganism.

An alkaline substance other than an ammonia or an amine may be added to the aqueous 1,4-butanediol-containing solution originated from a fermentation broth, and the resulting mixture distilled. By this process, colorless 1,4-butanediol with high purity suited for the production of polyesters can be obtained.

As the alkaline substance, alkaline metal hydroxides, alkaline metal salts, alkaline earth metal hydroxides and alkaline earth metal salts may preferably be used. Specific examples of these alkaline substances include alkaline metal hydroxides such as sodium hydroxide, potassium hydroxide and cesium hydroxide; alkaline earth metal hydroxides such as magnesium hydroxide, calcium hydroxide and barium hydroxide; alkaline metal carbonates and alkaline metal hydrogen carbonates such as sodium carbonate, sodium hydrogen carbonate, potassium carbonate, potassium hydrogen carbonate and cesium carbonate; and alkaline earth metal carbonates such as basic magnesium carbonate and calcium carbonate; as well as alkaline metal carboxylates such as sodium acetate and potassium acetate. Among these, hydroxides, carbonates and hydrogen carbonates of alkaline metals; and hydroxides and carbonates of alkaline earth metals are preferred, and sodium hydroxide, potassium hydroxide, sodium carbonate, potassium carbonate, calcium hydroxide and calcium carbonate are preferred because of the low price and high efficiency. The alkaline substance may be added in the form of solid or in the form of aqueous solution with which the amount of addition can be easily adjusted. The alkaline substance may be used individually or two or more alkaline substances may be used in combination.

Although the amount of addition of the alkaline substance is not restricted, if the amount of the added alkaline substance is too much, the distillation yield may be decreased. Therefore, the amount of addition of the alkaline substance is preferably not more than 20 mol %, more preferably not more than 10 mol %, still more preferably not more than 5 mol % based on the amount (number of moles) of 1,4-butanediol. The amount of addition of the alkaline substance can be determined by calculating the number of moles of 1,4-butanediol from the concentration of 1,4-butanediol. Although there is no particular lower limit of the amount of addition of the alkaline substance as long as the desired effect is obtained, the alkaline substance is preferably added in an amount of not less than 0.001 mol %, more preferably not less than 0.01 mol %, still more preferably not less than 0.1 mol % based on the amount (number of moles) of 1,4-butanediol.

In continuous distillation, the alkaline substance may be added in an amount based on the flow rate (mol/h) of the added alkaline substance calculated from the flow rate (mol/h) of 1,4-butanediol. Although the alkaline substance may be added to the 1,4-butanediol line, providing an addition/mixing vessel for addition of the alkaline substance is preferred because the addition of the alkaline substance can be attained more uniformly. U.S. Pat. No. 6,361,983 B and WO 2004/099110 teach that coloration is suppressed by adding an alkaline substance to the 1,3-butandiol solution such that a pH of 7 or more of the 1,3-butandiol solution is attained. In contrast, in our processes, since we confirmed that pH is not the cause of by-production of THF and the extension of the polymerization time during the production of polyesters, the desired effect can be obtained even when the pH is not more than 7.

When adding the alkaline substance, it is preferred to well stir the 1,4-butanediol solution. Although the action of the alkaline substance has not been elucidated, since the 1,4-butanediol solution has a high viscosity, it is preferred to stir the solution so that the reaction sufficiently proceeds. Although the solution may be heated because the viscosity is decreased and the reaction is accelerated thereby, since impurities may be generated at a high temperature, the temperature of the solution is preferably not higher than 150° C.

The distillation method of the aqueous 1,4-butanediol solution to which the alkaline substance was added is not restricted, and any of the usually used simple distillation, fractionating distillation, distillation under normal pressure and distillation under reduced pressure may be employed, and the distillation apparatus may be selected from thin film distillators, distillators with a plate column, distillators with a packed column and so on. Either batch distillation or continuous distillation can be employed. Among these, preferred is the distillation under reduced pressure because the boiling point can be lowered so that generation of impurities can be suppressed. More particularly, it is preferred to carry out the distillation at a temperature from 60° C. to 150° C. In cases where the temperature is lower than 60° C., since the pressure must be much lowered, maintenance of the distillation apparatus may be difficult on an industrial scale. On the other hand, when the temperature is higher than 150° C., impurities originated from the microbial fermentation remained in the aqueous 1,4-butanediol solution are decomposed and coloring substances are by-produced, which is not preferred. Thus, it is preferred to adjust the pressure so that 1,4-butanediol is distilled out within the temperature range mentioned above.

To decrease the load of the distillation equipment, a crude distillation may be carried out prior to addition of the alkaline substance. The crude distillation is carried out prior to the main distillation. Although the distillation method is not restricted, simple distillation is usually preferred because of the low cost. Crude distillation decreases the load of the main distillation equipment and contributes to the high purity of 1,4-butanediol. Thus, addition of the alkaline substance and the main distillation may be carried out after conducting the crude distillation.

Before adding the alkaline substance to the aqueous 1,4-butanediol-containing solution originated from a fermentation broth and distilling the resulting mixture, the aqueous 1,4-butanediol-containing solution originated from a fermentation broth may be subjected to treatments with a nanofiltration membrane, and/or ion exchange treatments, and/or concentration with a reverse osmosis membrane, thereby 1,4-butanediol having a higher purity can be obtained at a low cost. That is, by subjecting the aqueous 1,4-butanediol-containing solution originated from a fermentation broth to treatments with a nanofiltration membrane and ion exchange treatments to separate the impurities from 1,4-butanediol, generation of the distillation residue in the later distillation step can be suppressed so that the distillation yield can be increased and the quality of the purified product can be promoted and, by concentration with a reverse osmosis membrane, the aqueous 1,4-butanediol-containing solution originated from a fermentation broth can be concentrated with a small energy.

JP 2010-150248 A filters aqueous 1,4-butanediol-containing solution (not an actual fermentation broth) through the nanofiltration membrane, and 1,4-butanediol is separated to the permeate flow and the inorganic salts, saccharides and colored components are separated to the feed flow with a small energy efficiently. Highly pure 1,4-butanediol is preferably obtained by nanofiltration treatment followed by distillation with added alkaline substance.

Examples of the material constituting the known nanofiltration membranes include polymeric materials such as piperazine polyamide, polyamide, cellulose acetate, polyvinyl alcohol, polyimide and polyester; and inorganic materials such as ceramics. Nanofiltration membranes generally used are in the form of a spiral-wound membrane, flat membrane or hollow fiber membrane, and the nanofiltration membrane is preferably in the form of a spiral-wound membrane.

Specific examples of the nanofiltration membrane element include "GEsepa" commercially available from GE OSMONICS which is a cellulose acetate-based nanofiltration membrane; NF99 and NF99HF commercially available from ALFA-LAVAL which have a polyamide functional layer; NF-45, NF-90, NF-200 and NF-400 commercially available from FILMTEC which have a crosslinked piperazine polyamide functional layer; and nanofiltration membrane elements SU-210, SU-220, SU-600 and SU-610 containing a nanofiltration membrane UTC60 commercially available from TORAY INDUSTRIES, INC. which has a crosslinked piperazine polyamide functional layer. Among these, preferred are NF99 and NF99HF commercially available from ALFA-LAVAL which have a polyamide functional layer; NF-45, NF-90, NF-200 and NF-400 commercially available from FILMTEC which have a crosslinked piperazine polyamide functional layer; and nanofiltration membrane elements SU-210, SU-220, SU-600 and SU-610 containing a nanofiltration membrane UTC60 commercially available from TORAY INDUSTRIES, INC. which has a crosslinked piperazine polyamide functional layer. Among these, especially preferred are nanofiltration membrane elements SU-210, SU-220, SU-600 and SU-610 containing a nanofiltration membrane UTC60 commercially available from TORAY INDUSTRIES, INC. which has a crosslinked piperazine polyamide functional layer.

The filtration through the nanofiltration membrane may be carried out with pressure. The filtration pressure is preferably 0.1 MPa to 8 MPa. With a filtration pressure lower than 0.1 MPa, the membrane permeation flux may decrease, and with a filtration pressure higher than 8 MPa, the membrane may be damaged. A filtration pressure of 0.5 MPa to 7 MPa is more preferred because the aqueous 1,4-butanediol-containing solution can be efficiently filtered because of the high permeate flux, and the possibility of damaging the membrane is small. A filtration pressure of 1 MPa to 6 MPa is especially preferred.

Although the concentration of the aqueous 1,4-butanediol-containing solution to be filtered through the nanofiltration membrane is not restricted, a high concentration is preferred because the concentration of 1,4-butanediol in the permeate flow is also high so that the energy and, in turn, the cost to concentrate 1,4-butanediol can be lowered. The concentration of 1,4-butanediol in the feed flow may usually be, for example, from 0.5 wt % to 30 wt %, preferably 2 wt % to 20 wt %.

The ion exchange treatment removes ionic components in the aqueous 1,4-butanediol-containing solution using one or more ion exchangers. Examples of the ion exchanger include ion exchange resins, ion exchange membranes, ion exchange fibers, ion exchange papers, gel ion exchangers, liquid ion exchangers, carbonaceous ion exchangers and montmorillonite. Treatments using one or more ion exchange resins are preferably employed.

Ion exchange resins include, depending on the functional groups thereon, strong anion exchange resins, weak anion exchange resins, strong cation exchange resins, weak cation exchange resins and chelate exchange resins. Examples of the strong anion exchange resin include "Amberlite" IRA410J, IRA411 and IRA910CT commercially available from ORGANO and "Diaion" SA10A, SA12A, SA11A, NSA100, SA20A, SA21A, UBK510L, UBK530, UBK550, UBK535 and UBK555 commercially available from MITSUBISHI CHEMICALS. Examples of the weak anion exchange resin include "Amberlite" IRA478RF, IRA67, IRA96SB, IRA98 and XE583 commercially available from ORGANO and "Diaion" WA10, WA20, WA21J and WA30 commercially available from MITSUBISHI CHEMICALS. On the other hand, examples of the strong cation exchange resin include "Amberlite" IR120B, IR124, 200CT and 252 commercially available from ORGANO, and "Diaion" SK104, SK1B, SK110, SK112, PK208, PK212, PK216, PK218, PK220 and PK228 commercially available from MITSUBISHI CHEMICALS. Examples of the weak cation exchange resin include "Amberlite" FPC3500 and IRC76 commercially available from ORGANO, and "Diaion" WK10, WK11, WK100 and WK40L.

It is preferred to desalt the solution using both of one or more anion exchange resins and one or more cation exchange resins. It is especially preferred to use both of one or more strong anion exchange resins and one or more strong cation exchange resins, by which various ions can be removed. The anion exchange resins are preferably used as "OH type" after regeneration with a dilute aqueous alkaline solution such as aqueous sodium hydroxide solution. The cation exchange resins are preferably used as "H type" after regeneration with a dilute aqueous acid solution such as hydrochloric acid. Any desalting method using one or more exchange resins may be employed as long as the desalting can be attained efficiently, and either a batch process or a column process can be employed. A column process is preferably employed because the process can be repeated easily. The flow rate through the ion exchange resin is usually controlled by SV (space velocity), and an SV of 2 to 50, especially 2 to 10 is preferred by which a higher degree of purification may be attained. Commercially available ion exchange resins in the form of gel include porous type, high porous type and MR type. Any of these ion exchange resins having an arbitrary shape may be employed. A preferred shape can be selected depending on the quality of the solution.

Although the order of the treatment with the nanofiltration membrane and the ion exchange treatment is not restricted, it is preferred to first conduct the treatment with the nanofiltration membrane and apply the 1,4-butanediol-containing solution recovered from the permeate flow of the nanofiltration membrane in which the inorganic salts have been decreased to the ion exchange treatment. According to this method, by removing the inorganic salts and organic acids which passed through the nanofiltration membrane by the ion exchange treatment, the removal rate of the ionic impurities such as inorganic salts can be increased.

When the alkaline substance is added and distillation conducted, it is preferred to preliminarily concentrate the aqueous 1,4-butanediol-containing solution to promote the effect of the distillation. Although the concentration of 1,4-butanediol after the concentration is not restricted, a concentration of not less than 50% by weight is preferred to decrease the load of the distillation. On the other hand, since the solution preferably contains water to increase the solubility of the alkaline substance, the concentration of 1,4-butanediol is preferably less than 99% by weight.

As the method of concentrating the aqueous 1,4-butanediol-containing solution, usual known methods, including methods using a reverse osmosis membrane, concentration under heat by an evaporator, and evaporation methods, can be employed. A method using a reverse osmosis membrane is preferably employed.

The method using a reverse osmosis membrane is a method wherein the aqueous 1,4-butanediol-containing solution is filtered through the reverse osmosis membrane to permeate water through the membrane and to retain 1,4-butanediol in the feed flow. Preferred examples of the reverse osmosis membrane include composite membranes having a functional layer made of a cellulose acetate-based polymer (hereinafter also referred to as "cellulose acetate-based reverse osmosis membrane") and composite membranes having a functional layer made of a polyamide (hereinafter also referred to as "polyamide-based reverse osmosis membrane"). Examples of the cellulose acetate polymer include polymers prepared with organic acid esters of cellulose such as cellulose acetate, cellulose diacetate, cellulose triacetate, cellulose propionate and cellulose butyrate, which may be used solely, as a mixture, or as a mixed ester. Examples of the polyamide include linear polymers and cross-linked polymers constituted by aliphatic and/or aromatic diamine monomers. Examples of the form of the membrane which may be used as appropriate include the flat membrane, spiral-wound membrane and hollow fiber membrane.

Specific examples of the reverse osmosis membrane include polyamide reverse osmosis membrane modules commercially available from TORAY INDUSTRIES, INC., such as low-pressure type modules SU-710, SU-720, SU-720F, SU-710L, SU-720L, SU-720LF, SU-720R, SU-710P and SU-720P, as well as high-pressure type modules SU-810, SU-820, SU-820L and SU-820FA containing UTC70 as the reverse osmosis membrane; cellulose acetate reverse osmosis membranes commercially available from the same manufacturer SC-L100R, SC-L200R, SC-1100, SC-1200, SC-2100, SC-2200, SC-3100, SC-3200, SC-8100 and SC-8200; NTR-759HR, NTR-729HF, NTR-70SWC, ES10-D, ES20-D, ES20-U, ES15-D, ES15-U and LF10-D commercially available from Nitto Denko Corporation; RO98pHt, R099, HR98PP and CE4040C-30D commercially available from ALFA-LAVAL; GE Sepa commercially available from GE; and BW30-4040, TW30-4040, XLE-4040, LP-4040, LE-4040, SW30-4040 and SW30HRLE-4040 commercially available from FILMTEC CORPORATION.

Concentration with the reverse osmosis membrane is carried out under pressure, and the filtration pressure is preferably 1 MPa to 8 MPa since, with a filtration pressure lower than 1 MPa, the membrane permeation flux may decrease, and with a filtration pressure higher than 8 MPa, the membrane may be damaged. Further, since, with a filtration pressure within the range of 1 MPa to 7 MPa, the membrane permeation flux is high, the aqueous 1,4-butanediol-containing solution can be efficiently concentrated. The filtration pressure is most preferably 2 MPa to 6 MPa since there is less possibility of causing damage to the membrane in this case. When the aqueous 1,4-butanediol-containing solution has a low concentration, the method of using the reverse osmosis membrane is preferred because of the low cost.

The dicarboxylic acid used as a material to produce polyesters together with the 1,4-butanediol may be any of the one synthesized by a petroleum chemical method (organic synthesis method), produced by a microorganism by a fermentation method and produced by the combination of the petroleum chemical method and the fermentation method.

Examples of the dicarboxylic acid include aromatic dicarboxylic acids, aliphatic dicarboxylic acids and alicyclic dicarboxylic acid. Specific examples of the aromatic dicarboxylic acid include terephthalic acid, isophthalic acid, naphthalene dicarboxylic acid, phthalic acid, diphenyldicarboxylic acid, diphenyletherdicarboxylic acid, diphenoxyethane dicarboxylic acid, 5-sodium sulfoisophthalic acid. Specific examples of the aliphatic dicarboxylic acid include oxalic acid, succinic acid, adipic acid, sebacic acid, dimer acid and maleic acid. Specific examples of the alicyclic dicarboxylic acid include 1,4-cyclohexanedicarboxylic acid and decalin dicarboxylic acid. The above-described dicarboxylic acid may be a dicarboxylic acid obtained by fermentation of a biomass. For example, the dicarboxylic acid may be succinic acid obtained by growing a recombinant *Brebibacterium fulavum* which is an aerobic coryneform bacterium and contacting the *Brebibacterium fulavum* with an organic material anaerobically in a carbon dioxide-containing solution (JP 11-196888 A). The dicarboxylic acid may also be one obtained by a combination of a chemical reaction and an enzyme reaction using a biomass or a microbial fermentation product as a precursor. For example, the dicarboxylic acid may be the oxalic acid obtained by an enzyme reaction of an oxamide (JP 5-38291 A), or the adipic acid obtained by hydrogenation reaction of muconic acid by a recombinant *Escherichia coli* (Journal of American Chemical Society No. 116 (1994) 399-400) or the sebacic acid obtained from castor oil. Although any of these dicarboxylic acids may preferably be employed, the dicarboxylic acid is preferably an aromatic dicarboxylic acid, and most preferably, terephthalic acid.

As the method of producing a polyester using the obtained 1,4-butanediol and the dicarboxylic acid, known methods can be used as they are. For example, a polyester can be produced by, for example, an esterification reaction or an ester exchange reaction between 1,4-butanediol and the dicarboxylic acid or a dicarboxylic acid component which is an ester-forming derivative of the dicarboxylic acid; and by subsequent polycondensation reaction. Although the reaction may be either a solution reaction using a solvent or a melt reaction, melt reaction is preferred because a polyester with a high quality can be obtained. The catalyst and the solvent used in the reaction may be controlled for 1,4-butanediol and the dicarboxylic acid component. More particularly, known production processes of polyesters include ester exchange reaction process and direct polymerization process. The process of producing a polyester may be any of the ester exchange method wherein a dialkyl ester of an aromatic dicarboxylic acid and the 1,4-butanediol produced by our processes are used; a method wherein an ester between an aromatic dicarboxylic acid and 1,4-butanediol is synthesized and then a polycondensation reaction is carried out; and a direct polymerization method between an aliphatic dicarboxylic acid and the 1,4-butanediol produced by our processes. The esterification reaction or the ester exchange reaction, and the subsequent polycondensation reaction may be carried out as a batch process or a continuous process. In each of these reactions, the reactor is not restricted, and a stirrer type reactor, mixer type reactor, tower type reactor, extruder type reactor and so on may be employed. The reactor may be used individually or two or more of the reactors may be used in combination.

We discovered that the amount of the by-produced tetrahydrofuran (THF) is large when 1,4-butanediol originated from a fermentation broth in which impurities had not been insufficiently removed and a dicarboxylic acid are subjected to an esterification reaction. THF is produced by intramolecular dehydration reaction of 1,4-butanediol, and possibly an impurity originated from the microbial fermentation accelerated this side reaction. An increase in the amount of the by-produced THF means a breakage of the molar balance between 1,4-butanediol and the dicarboxylic acid which are the materials, and an increase in the amount of fed 1,4-butanediol and extension of the reaction time are necessitated so that the costs are increased. By using the obtained 1,4-butanediol, by-production of THF during the esterification reaction can be prominently suppressed. We also discovered that when a polycondensation reaction is carried out after the esterification reaction using the 1,4-butanediol originated from a fermentation broth, the polymerization time is extended. Extension of the polymerization time may necessitate the change of the reaction conditions such as heating temperature and heating time, and increase in the catalyst added so that it may influence on the productivity and economy of the process. Since the extension of the polymerization time can be suppressed by using the obtained 1,4-butanediol, the obtained 1,4-butanediol can be suitably used as a polyester material.

The esterification reaction or the ester exchange reaction, and the subsequent polycondensation reaction may be accelerated by using a catalyst. Preferred examples of the compound used as the catalyst include titanium compounds, tin compounds, aluminum compounds, calcium compounds, lithium compounds, magnesium compounds, cobalt compounds, manganese compounds, antimony compounds, germanium compounds and zinc compounds. These compounds are preferred because the reactivity is high so that the rate of reaction and the yield of the polyester can be increased. Example of the catalyst of the ester exchange reaction include alkaline metal acetates, and examples of the polymerization catalyst include germanium oxide and antimony oxide in which the contamination with bismuth is small, as well as compounds of transition metals such as cobalt and alkoxy titanates. In view of the fact that the reaction time can be shortened and the polyester can be produced efficiently, titan compounds, tin compounds, aluminum compounds, antimony compounds and germanium compounds are preferred. Among these, in view of the fact that the crystallization characteristics can be easily controlled and that a polyester having an excellent heat stability, hydrolysis resistance and thermal conductivity can be obtained, titanium compounds and/or tin compounds are preferred, and titanium compounds are more preferred because the load on the environment is small. Examples of the titanium compounds include titanic acid esters such as tetra-n-propyl ester, tetra-n-butyl ester, tetraisopropyl ester, tetraisobutyl ester, tetra-tert-butyl ester, cyclohexyl ester, phenyl ester, benzyl ester and tolyl ester, as well as mixed esters of these esters. Among these, in view of the fact that a polyester resin can be produced efficiently, tetrapropyl titanate, tetrabutyl titanate and tetraisopropyl titanate are preferred, and tetra-n-butyl titanate is especially preferred. Examples of the tin compounds include monobutyltin oxide, dibutyltin oxide, methylphenyltin oxide, tetraethyltin oxide, hexaethyl-di-tin oxide, cyclohexahexyl di-tin oxide, didodecyltin oxide, triethyltin hydroxide, triphenyltin hydroxide, triisobutyltin acetate, dibutyltin diacetate, diphenyltin dilaurate, monobutyltin trichloride, dibutyltin dichloride, tributyltin chloride, dibutyltin sulfide and butylhydroxytin oxide, methyl stannonic acid, ethyl stannonic acid and butyl stannonic acid. Among these, in views of the fact that the polyester can be produced efficiently, monoalkyl tin compounds are preferably employed. These compounds serving as a catalyst may be used individually or two or more compounds may be used in combination in the esterification reaction or ester exchange reaction and in the subsequent polycondensation reaction. The catalyst may be added immediately after the addition of the materials, or may be added together with the materials, or may be added during the reaction. As for the amount of the catalyst added, in cases where the catalyst is a titanium compound, the amount of added catalyst is preferably 0.01 to 0.3 parts by weight with respect to 100 parts by weight of the polyester to be produced, and in view of the heat stability, hue and reactivity, an amount of 0.02 to 0.2 parts by weight is more preferred, and an amount of 0.03 to 0.15 parts by weight is still more preferred.

In the production of a polyester, to improve the heat resistance, hue, weatherability and durability, one or more usual additives such as ultraviolet absorbers, heat stabilizers, lubricants, releasing agents, coloring agents containing a dye or a pigment may be added in an amount not adversely affecting the desired effect.

The obtained polyesters are obtained by using as materials the 1,4-butanediol and the dicarboxylic acid. Specific examples of the polyester include the polyesters obtained by the reaction of the 1,4-butanediol with succinic acid, with adipic acid, with succinic acid and adipic acid (polybutylene succinate adipate), with oxalic acid, with sebacic acid, with terephthalic acid (polybutylene terephthalate), with succinic acid and terephthalic acid (polybutylene succinate terephthalate), and with naphthalene dicarboxylic acid (polybutylene naphthalate).

A process of producing a polyester copolymer by using as a material a third or more copolymerization components is included within the scope of the process of producing a polyester. Examples of the copolymerization component include bifunctional oxycarboxylic acids, and to form a crosslinking structure, at least one selected from the group consisting of tri- or more functional polyhydric alcohols, tri- or more functional carboxylic acids and anhydrates thereof, and tri- or more functional oxycarboxylic acids. Using, among these, a tri- or more oxycarboxylic acid is most preferred because a polyester having a high degree of polymerization can be obtained with a very small amount without using a chain extender. Examples of the polyester copolymer include polyesters containing as a third component lactic acid (e.g., polybutylene succinate lactate) and polyesters containing as a third component bisphenol A (e.g., polybutylene succinate carbonate).

By blending one or more widely used thermoplastic resins with the obtained polyester and the resulting resin compositions can be used in various uses. Examples of the widely used thermoplastic resins include polyolefin resins such as polyethylene, polypropylene, ethylene-vinyl acetate copolymer and ethylene-α-olefin copolymers; halogen-containing resins such as polyvinyl chloride, polyvinylidene chloride, chlorinated polyolefins and polyvinylidene fluoride; polystyrene resins such as polystyrene and acrylonitrile-butadiene-styrene copolymer; polyester resins such as polyethylene terephthalate and polybutylene terephthalate; elastomers such as polyisoprene, polybutadiene, acrylonitrile-butadiene copolymers and styrene-isoprene copolymers; and polyamide resins such as nylon 6,6 and nylon 6; as well as polyvinyl chloride, methacrylate resins, polycarbonate resins, polyacetal, polyphenylene oxide ad polyurethane. The various characteristics of the resin composition may be adjusted by using one or more various compatibilizing agent.

Further, by blending one or more known additives with the obtained polyester, the composition can be used in various uses. Examples of the additives for resins include crystal nucleating agents, antioxidants, anti-blocking agents, UV absorbers, photostabilizers, plasticizers, heat stabilizers, coloring agents, flame retardants, releasing agents, antistatic agents, anti-fogging agents, surface wetting improvers, incineration aids, pigments, lubricants, dispersion aids and various surfactants.

Further, by blending one or more known fillers with the obtained polyester, the composition can be used in various applications.

Examples of inorganic filler include, anhydrous silica, mica, talc, titanium oxide, calcium carbonate, diatomaceous earth, allophane, bentonite, potassium titanate, zeolite, sepiolite, smectite, kaolin, kaolinite, glass fibers, limestone, carbon, wollastonite, sintered perlite, silicates such as calcium silicate and sodium silicate, aluminum oxide, magnesium carbonate, hydroxides such as calcium hydroxide, ferric carbonate, zinc oxide, iron oxide and salts such as aluminum phosphate and barium sulfate.

Examples of organic fillers include, raw starch, processed starch, pulp, chitin and chitosan materials, coconut husk powder, wood powder, bamboo powder, bark powder, and powders of kenaf and straw.

Preparation of the above-described composition can be carried out by any of the known mixing/kneading techniques. As the mixer, horizontal cylinder mixers, V-shaped mixers, double conical mixers, blenders such as ribbon blenders and super mixers, and various continuous mixers can be used. As the kneader, batch kneaders such as roll and internal mixers, one-step type and two-step type continuous kneaders, double-screw extruders, single-screw extruders and the like can be used. The kneading may be carried out by, for example, heating the composition to melt, adding thereto the various additives, fillers and thermoplastic resins, and kneading the resulting mixture. An oil for blending may also be used to uniformly disperse the various additives.

By subjecting the obtained polyester to a known molding method, a molded product can be obtained. Examples of the known molding method include compression molding (compression molding, laminate molding, stampable molding), injection molding, extrusion molding and co-extrusion molding (molding of films by inflation method and T-die method, molding of laminate films, molding of sheets, molding of pipes, molding of wires/cables, and molding of profile), various blow moldings, calender molding, foam molding (meld foam molding, solid phase foam molding), solid molding (uniaxial stretching molding, biaxial stretching molding, roll molding, molding of stretched and oriented non-woven fabrics, heat forming (vacuum forming, pressure forming), plastic working), powder molding (rotational molding), forming of various non-woven fabric (dry method, adhesion method, slipping method, spunbonding method) and the like.

By these molding methods, various molded or formed articles including monolayer films, multilayer films, oriented films, shrink films, laminate films, monolayer sheets, multilayer sheets, stretched sheets, pipes, wires/cables, monofilaments, multifilaments, various non-woven fabrics, flat yarn, staple, textured fibers, stretched tapes and bands, striped tapes, split yarns, composite fibers, blow bottles and foam products are obtained. The obtained molded or formed articles are expected to be applied to various uses including various films such as shopping bags, trash bags, and films for agriculture; various containers such as containers of cosmetics, detergents, foods and bleaching agents; fabrics, fishing lines, fishing nets, ropes, tying materials and ligatures, sanitary cover stock materials, cooler bags, buffer materials, medical materials, electrical equipment materials, consumer electronics housings, materials of automobiles, civil engineering and construction materials and stationeries.

EXAMPLES

Our processes will now be described by way of Examples thereof. It should be noted that the Examples are presented for the illustration purpose only and should not be interpreted in any restrictive way.

The characteristic values of 1,4-butanediol (hereinafter also referred to as "1,4-BDO") and the amounts of the by-produced THF during the esterification reaction in these Examples were obtained by the following measurement methods:

A. Purity of 1,4-Butanediol

After analyzing the 1,4-butanediol after the distillation by gas chromatography (GC) using a GC system commercially available from SHIMADZU CORPORATOIN), the purity (GC purity) of 1,4-butanediol was calculated by the Equation 1 below from the ratio of the area of the peak of 1,4-butanediol to the total area of the detected peaks:

$$\text{GC Purity (\%)}=100\times(\text{area of 1,4-BDO peak})/(\text{total area of the detected peaks}) \quad (1).$$

The analysis conditions of the gas chromatography were as follows:
Column: RT-BDEXM (0.25 mm×30 m, commercially available from RESTEK)
Column temperature: 75° C.
Temperature of vaporizing chamber and detector: 230° C.
Carrier gas: He
Linear velocity: 35 cm/sec
Detection: hydrogen flame ionization detector (FID).

B. Degree of Pigmentation (APHA)

1,4-butanediol after distillation was analyzed with a colorimeter (commercially available from NIPPON DENSHOKU INDUSTRIES) to determine the APHA unit color number.

C. Total Ion Concentration

Ion concentrations were measured by an ion chromatography (commercially available from DIONEX), and the total of the concentrations of $Na$, $NH_4$, $K$, $Cl$, $PO_4$ and $SO_4$ ions were defined as total ion concentration.
Measurement of Anion Concentration
Column: AS4A-SC (commercially available from DIONEX)
Column Temperature: 35° C.
Eluent: 1.8 mM sodium carbonate/1.7 mM sodium hydrogen carbonate
Detection: electric conductivity
Measurement of Cation Concentration
Column: CS12A (commercially available from DIONEX)
Column Temperature: 35° C.
Eluent: 20 mM methanesulfonic acid
Detection: electric conductivity D. Amount of by-Produced THF During Esterification Reaction The amount of the by-produced THF (g/kg PBT) was calculated by the following Equations 2 to 4 based on the measurement results of the amount of the distillate and the density of the distillate during the esterification reaction:

$$\text{Amount of by-produced THF (g/kg PBT)}=1000\times\{\text{amount of produced THF (g) during esterification reaction}\}/\{\text{amount of polymer (g)}\} \quad (2)$$

$$\text{Amount of by-produced THF (g) during esterification reaction}=\{\text{amount of distillate (g)/density of distillate (g/ml)}\}\times 0.889\times\{1-\text{density of distillate (g/ml)}\}/(1-0.889) \quad (3)$$

$$\text{Amount of polymer (g)}=(\text{number of moles of fed dicarboxylic acid})\times\{(\text{molecular weight of dicarboxylic acid})+(\text{molecular weight of 1,4-butanediol})-(\text{molecular weight of water}\times 2)\}/\{1-\text{amount of catalyst (wt \% based on polymer)}/100\} \quad (4).$$

Examples 1 to 4 and Comparative Example 1

Distillation of Model Fermentation Broth with Added Alkaline Substance and Evaluation of Esterification Reaction Between 1,4-Butanediol and Dicarboxylic Acid Preparation of Model Fermentation Broth Containing 1,4-Butanediol To ultrapure water, 1,4-butanediol, γ-butyrolactone, acetic acid, glucose, fructose, sucrose, sodium chloride, ammonium sulfate, potassium hydrogen phosphate and hydrochloric acid were added to prepare the aqueous 1,4-butanediol solution having the composition shown in Table 1, which solution was used as the model fermentation broth.

TABLE 1

| Component | Concentration (wt %) |
|---|---|
| Water | 78.39 |
| 1,4-BOD | 13.9 |
| γ-butyrolactone | 3.11 |
| Acetic Acid | 0.58 |
| Glucose | 0.18 |

TABLE 1-continued

| Component | Concentration (wt %) |
|---|---|
| Fructose | 0.12 |
| Sucrose | 0.28 |
| Na | 1.57 |

TABLE 1-continued

| Component | Concentration (wt %) |
|---|---|
| $NH_4$ | 0.03 |
| K | 0.62 |
| Cl | 0.55 |
| $PO_4$ | 0.62 |
| $SO_4$ | 0.17 |

Distillation of Model Fermentation Broth with Added Alkaline Substance

The above-described fermentation broth was concentrated by a thin film concentrator MF-10 (commercially available from TOKYO RIKAKIKAI) at a reduced pressure of 30 hPa and at a raised temperature of 60° C. to obtain an aqueous 50 wt % 1,4-butanediol solution. To 500 g of the concentrated 1,4-butanediol solution, 1.33 g (1.2 mol % based on the amount (number of moles) of 1,4-butanediol, Example 1), 2.33 g (2.1 mol % based on the amount (number of moles) of 1,4-butanediol, Example 2), 2.45 g (2.2 mol % based on the amount (number of moles) of 1,4-butanediol, Example 3) or 4.23 g (3.8 mol % based on the amount (number of moles) of 1,4-butanediol, Example 4) of sodium hydroxide was added and the resulting solution was well stirred until sodium hydroxide is dissolved. The resulting solution was subjected to distillation under reduced pressure (5 mmHg) at 110° C. to obtain purified 1,4-butanediol. The analytical results of the obtained 1,4-butanediol for the GC purity, degree of pigmentation (APHA) and the total ion concentration are shown in Table 2. The results obtained by carrying out the same operations except that sodium hydroxide was not added are also shown as Comparative Example 1.

Esterification Reaction Between 1,4-Butanediol and Dicarboxylic Acid

To carry out the esterification reaction, 122.7 g of 1,4-butanediol after distillation and 113.2 g of terephthalic acid (commercially available from WAKO PURE CHEMICAL INDUSTRIES) were mixed, and 0.08 g of tetra-n-butyl titanate and 0.07 g of monobutylhydroxy tin oxide as catalysts were added to the resulting mixture. The reaction mixture was placed in a reactor with a rectifying column and the reaction was started at 190° C., 79.9 kPa. The reaction was carried out for 270 minutes while raising the temperature stepwise to obtain an esterification reaction product. The density of the distillate obtained during the esterification reaction was measured to determine the THF content in the distillate, and the amount of the by-produced THF (g/kg PBT) was calculated according to the Equations 2 to 4. As Comparative Example 1, the esterification reaction was carried out in the same manner as described above for the 1,4-butanediol obtained by the same operations except that sodium hydroxide was not added. The results are shown in Table 2.

TABLE 2

| | | Comparative Example 1 | Example 1 | Example 2 | Example 3 | Example 4 |
|---|---|---|---|---|---|---|
| | Amount of added alkaline substance [mol % based on 1,4-BDO] | 0 | 1.2 | 2.1 | 2.2 | 3.8 |
| Quality of 1,4-BOD after distillation | GC purity [%] | 94.9 | 95.8 | 97.4 | 97.2 | 99.9 |
| | Degree of pigmentation | 75 | 66 | 51 | 35 | 23 |
| | Total ion concentration [ppm] | 340 | 5 | 3 | 2 | 1 |
| Esterification | Completion of reaction | No | Yes | Yes | Yes | Yes |
| | Amount of by-produced THF [g/kg PBT] | 115 | 59 | 50 | 55 | 65 |

As shown in Table 2, with the increase in the amount of the added alkaline substance, the purity of 1,4-butanediol after distillation is increased and the degree of pigmentation is decreased. It was also shown that the amount of the by-produced THF during the reaction can be decreased by using as a material of the esterification reaction the 1,4-butanediol obtained by the distillation after adding the alkaline substance. On the other hand, in Comparative Example 1, even after the esterification reaction for a prescribed time, unreacted terephthalic acid remained in suspended condition so that the esterification reaction was not completed.

Examples 5 and 6, and Comparative Example 2

Treatment with Nanofiltration Membrane, Concentration with Reverse Osmosis Membrane, Ion Exchange Treatment and Purification by Distillation with Added Alkaline Substance of Fermentation Broth Containing 1,4-Butanediol, and Evaluation of Esterification Reaction of Obtained 1,4-Butanediol and Dicarboxylic Acid Preparation of 1,4-Butanediol Fermentation Broth A fermentation broth sample containing 1,4-butanediol produced by microbial fermentation was obtained (for example, see WO 2008/115840). 27 L of fermentation broth was employed.

Treatment with Nanofiltration Membrane of Fermentation Broth Containing 1,4-Butanediol The above-described fermentation broth was purified with the membrane separation apparatus shown in FIG. 1. In FIG. 1, reference numeral 1 denotes a feed tank; reference numeral 2 denotes a vessel in which a nanofiltration membrane or a reverse osmosis membrane was mounted; reference numeral 3 denotes a high pressure pump; reference numeral 4 denotes the flow of the membrane permeate; reference numeral 5 denotes the flow of the concentrated solution; and reference numeral 6 denotes the flow of the aqueous 1,4-butanediol-containing solution driven by a high pressure pump. As a nanofiltration membrane 2, a spiral type membrane element "SU-610" (commercially available from TORAY INDUSTRIES, INC.) was used. The above-described fermentation broth containing 1,4-butanediol was fed to a feed tank 1, and the apparatus was driven at a feed flow rate of 18 L/min, a feed water pressure of 5 MPa and a feed water temperature of 18° C. to carry out the purification with a nanofiltration membrane. The obtained permeate 4 was a clear 1,4-butanediol solution from which colored components have been removed.

Concentration with Reverse Osmosis Membrane of Aqueous 1,4-Butanediol Solution Obtained by Nanofiltration Membrane Treatment As the membrane 2 shown in FIG. 1, a reverse osmosis membrane which was a spiral-wound membrane element "TM-810" (commercially available from TORAY INDUSTRIES, INC.) was used. The permeate through the above-described nanofiltration membrane was fed to the feed tank 1, and the apparatus was driven at a feed water pressure of 5 MPa and a feed water temperature of 18° C. to remove the water to the permeate flow of the membrane to carry out the concentration of 1,4-butanediol by the reverse osmosis membrane. After driving the apparatus, a 1,4-butanediol concentrate was recovered from the tank 1.

Ion Exchange Treatment of Aqueous 1,4-Butanediol Concentrated with Reverse Osmosis Membrane The 1,4-butanediol concentrate obtained by the above-described concentration with the reverse osmosis membrane was subjected to an ion exchange treatment to remove the residual ions. A strong cation exchange resin "IR410J" (commercially available from ORGANO) and a strong anion exchange resin "IR120" (commercially available from ORGANO) were used. These ion exchange resins were used after regeneration to OH type and H type, respectively, by treatments with 1N sodium hydroxide and 1N hydrochloric acid, respectively. The amounts of the resins were calculated such that the total amount of the various inorganic salts and organic acid salts was equal to the ion exchange capacities of the resins, respectively. The respective above-described ion exchange resins were packed into columns, and the solution was made to pass through the anion exchange column and then through the cation exchange column at a flow rate SV=10.

Distillation of Aqueous 1,4-Butanediol Solution after Ion Exchange Treatment with Added Alkaline Substance The aqueous 1,4-butanediol solution after the ion exchange treatment was concentrated by a thin film concentrator MF-10 (commercially available from TOKYO RIKAKIKAI) at a reduced pressure of 30 hPa and at a raised temperature of 60° C. to obtain an aqueous 50 wt % 1,4-butanediol solution. To 500 g of the concentrated 1,4-butanediol solution, 3.00 g of sodium hydroxide (2.7 mol % based on the amount (number of moles) of 1,4-butanediol, Example 5) or 7.00 g (6.3 mol % based on the amount (number of moles) of 1,4-butanediol, Example 6) of sodium hydroxide was added and the resulting solution was well stirred until sodium hydroxide is dissolved. The resulting solution was subjected to distillation under reduced pressure (5 mmHg) at 110° C. to obtain purified 1,4-butanediol. The analytical results of the obtained 1,4-butanediol for the GC purity, degree of pigmentation (APHA) and total ion concentration are shown in Table 3. The results obtained by carrying out the same operations except that sodium hydroxide was not added are also shown as Comparative Example 2.

Esterification Reaction Between Distilled 1,4-Butanediol and Dicarboxylic Acid

Using the 1,4-butanediol after the above-described distillation, an esterification reaction was carried out in the same manner as in Examples 1 to 4 to obtain an esterification reaction product. The amount of the by-produced THF (g/kg PBT) was calculated in the same manner as in Examples 1 to 4. As Comparative Example 2, the esterification reaction was carried out in the same manner as described above for the 1,4-butanediol obtained by the same operations except that sodium hydroxide was not added. The results are shown in Table 3.

Evaluation of Esterification Reaction Between 1,4-Butanediol Originated from Petroleum and Dicarboxylic Acid A commercially available 1,4-butanediol (WAKO PURE CHEMICALS) originated from petroleum was analyzed for the GC purity, degree of pigmentation (APHA) and the total ion concentration, and subjected to the esterification reaction to calculate the amount of the by-produced THF (g/kg PBT) during the esterification reaction in the same manner as in Examples 5 and 6. The results are shown in Table 3.

TABLE 3

| | | Comparative Example 2 | Example 5 | Example 6 | Reference Example 1 |
|---|---|---|---|---|---|
| | Amount of added alkaline substance [mol % based on 1,4-BDO] | 0 | 2.7 | 6.3 | — |
| Quality of 1,4-BOD after distillation | GC purity [%] | 99.8 | 99.9 | 99.9 | 99.9 |
| | Degree of pigmentation | 7 | 3 | 3 | 5 |
| | Total ion concentration [ppm] | 2.6 | <0.1 | <0.1 | 0.1 |
| Esterification | Completion of reaction | No | Yes | Yes | Yes |
| | Amount of by-produced THF [g/kg PBT] | 327 | 68 | 83 | 88 |

As shown in Table 3, the purity and degree of pigmentation of the obtained 1,4-butanediol were improved by subjecting the 1,4-butanediol-containing fermentation broth to the treatment with the nanofiltration membrane, treatment with the reverse osmosis membrane, ion exchange treatment and subsequent distillation with an added alkaline substance. Further, it was shown that by carrying out the esterification reaction using as a material the 1,4-butanediol after the distillation with the added alkaline substance, the amount of the by-produced THF can be decreased to the same level as when the petroleum-derived 1,4-butanediol (Reference Example 1) was used. On the other hand, in Comparative Example 2, even after the esterification reaction for a prescribed time, unreacted terephthalic acid remained in suspended condition so that the esterification reaction was not completed.

Example 7 and Comparative Examples 3 and 4

Treatment with Nanofiltration Membrane, Concentration with Reverse Osmosis Membrane, Ion Exchange Treatment and Purification by Distillation with Added Alkaline Substance of 1,4-Butanediol-Containing Fermentation Broth, and Evaluation of Esterification Reaction and Polymerization of Obtained 1,4-Butanediol and Dicarboxylic Acid Preparation of 1,4-Butanediol Originated from Microbial Fermentation A 1,4-butanediol-containing fermentation broth produced by microbial fermentation was obtained (see WO 2008/

115840). The obtained fermentation broth was purified (see, for example, WO 2010/141780) to obtain partially purified 1,4-butanediol.

Distillation of Partially Purified 1,4-Butanediol with Added Alkaline Substance

Water was added to the above-described partially purified 1,4-butanediol to obtain a 80 wt % aqueous 1,4-butanediol solution. To 500 g of this 1,4-butanediol solution, 6.01 g (3.4 mol % based on the amount (number of moles) of 1,4-butanediol, Example 7) of sodium hydroxide was added and the resulting solution was well stirred until sodium hydroxide is dissolved. The resulting solution was subjected to distillation under reduced pressure (5 mmHg) at 110° C. to obtain purified 1,4-butanediol. The analytical results of the obtained 1,4-butanediol for the GC purity, degree of pigmentation (APHA) and total ion concentration are shown in Table 4. The results obtained by using the partially purified 1,4-butanediol as Comparative Example 3 and the results obtained by carrying out the same operations except that sodium hydroxide was not added are also shown as Comparative Example 4.

Esterification Reaction Between Distilled 1,4-Butanediol and Dicarboxylic Acid

To carry out the esterification reaction, 54.2 g of 1,4-butanediol after distillation and 113.2 g of terephthalic acid (commercially available from WAKO PURE CHEMICAL INDUSTRIES) were mixed, and 0.08 g of tetra-n-butyl titanate and 0.07 g of monobutylhydroxy tin oxide as catalysts were added to the resulting mixture. The reaction mixture was placed in a reactor with a rectifying column and the reaction was started at 190° C., 79.9 kPa. The reaction was carried out while raising the temperature stepwise and adding 19.5 g (final concentration by mole: 1,4-butanediol/terephthalic acid=1.2/1) to obtain an esterification reaction product. The amount of the by-produced THF (g/kg PBT) was calculated in the same manner as in Examples 1 to 4. As Comparative Example 3, the partially purified 1,4-butanediol, and as Comparative Example 4, the 1,4-butanediol obtained by the same operations as described above except that sodium hydroxide was not added were subjected to the esterification reaction, respectively. The results are shown in Table 4.

Polymerization Test of Esterification Reaction Product

To 125 g of the above-described esterification reaction product, 0.08 g of tetra-n-butyl titanate and 0.01 g of phosphoric acid as catalysts were added, and a polycondensation reaction was carried out at 250° C., 67 Pa. The progress of the reaction was confirmed by the increase in the torque measured by a torque meter connected to a stirrer, and the time required for the torque value to reach 4 kgf·cm was defined as the polymerization reaction time. The polymerization reaction time is shown in Table 4.

Reference Example 2

Evaluation of Esterification Reaction Between Petroleum-Derived 1,4-Butanediol and Dicarboxylic Acid, and Evaluation of Polymerization A commercially available 1,4-butanediol (WAKO PURE CHEMICALS) originated from petroleum was analyzed for the GC purity, degree of pigmentation (APHA) and the total ion concentration, subjected to the esterification reaction to calculate the amount of the by-produced THF (g/kg PBT) during the esterification reaction, and subjected to the polymerization test, in the same manner as in Example 7. The results are shown in Table 4.

TABLE 4

| | | Comparative Example 3 | Comparative Example 4 | Example 7 | Reference Example 2 |
|---|---|---|---|---|---|
| | Amount of added alkaline substance [mol % based on 1,4-BDO] | — | 0 | 3.4 | — |
| Quality of 1,4-BOD | GC purity [%] | 99.9 | 99.9 | 99.9 | 99.9 |
| | Degree of pigmentation | 6 | 3 | 3 | 5 |
| | Total ion concentration [ppm] | 5.6 | 2.0 | <0.1 | 0.1 |
| Esterification | Completion of reaction | No | Yes | Yes | Yes |
| | Amount of by-produced THF [g/kg PBT] | 18.9 | 13.0 | 10.0 | 12.3 |
| PBT polymerization | Polymerization time [min] | — | 165 | 150 | 145 |

As shown in Table 4, the esterification reaction using the partially purified 1,4-butanediol (Comparative Example 3) was not completed. When the sample obtained by distilling the partially purified 1,4-butanediol was used (Comparative Example 4), although the esterification reaction was completed, it was shown that a longer polymerization time was required than in the case where a sample obtained after distillation with the added alkaline substance was used (Example 7). It was also shown that the polymerization time when the 1,4-butanediol obtained after distillation with the added alkaline substance (Example 7) was used can be shortened to about the same level as the case where 1,4-butanediol (Reference Example 2) originated from petroleum was used.

Example 8 and Comparative Example 5

Distillation of Model Fermentation Broth with Added Alkaline Substance and Evaluation of Esterification Reaction Between 1,4-Butanediol and Dicarboxylic Acid Preparation of Model Fermentation Broth Containing 1,4-Butanediol To ultrapure water, 1,4-butanediol, γ-butyrolactone, acetic acid, glucose, fructose, sucrose, sodium chloride, ammonium sulfate, potassium hydrogen phosphate and hydrochloric acid were added to prepare the aqueous 1,4-butanediol solution having the composition shown in Table 5, which solution was used as the model fermentation broth.

TABLE 5

| component | concentration [wt %] |
|---|---|
| water | 79.8 |
| 1,4-BDO | 13.8 |
| γ-butyrolactone | 2.61 |
| Acetic acid | 0.58 |
| Glucose | 0.16 |
| Fructose | 0.12 |

TABLE 5-continued

| component | concentration [wt %] |
|---|---|
| Sucrose | 0.28 |
| Na | 1.32 |
| $NH_4$ | 0.03 |
| K | 0.63 |
| Cl | 0.53 |
| $PO_4$ | 0.58 |
| $SO_4$ | 0.16 |

Distillation of Model Fermentation Broth with Added Alkaline Substance

The above-described model fermentation broth (Table 5) was concentrated by a thin film concentrator MF-10 (commercially available from TOKYO RIKAKIKAI) at a reduced pressure of 30 hPa and at a raised temperature of 60° C. to obtain an aqueous 50 wt % 1,4-butanediol solution. To 200 g of the concentrated 1,4-butanediol solution, 0.75 g (1.7 mol % based on the amount (number of moles) of 1,4-butanediol, Example 8) of sodium hydroxide was added and the resulting solution was well stirred until sodium hydroxide was dissolved. The resulting solution was subjected to distillation under reduced pressure (1.3 mmHg) at 130° C. to obtain purified 1,4-butanediol. The analytical results of 1,4-butanediol for GC purity, degree of pigmentation (APHA) and the total ion concentration are shown in Table 6. The results obtained by carrying out the same operations except that sodium hydroxide was not added are also shown as Comparative Example 5.

Esterification Reaction Between 1,4-Butanediol and Dicarboxylic Acid

To carry out the esterification reaction, 62.7 g of 1,4-butanediol after distillation and 52.6 g of terephthalic acid (commercially available from WAKO PURE CHEMICAL INDUSTRIES) were mixed, and 0.04 g of tetra-n-butyl titanate and 0.03 g of monobutylhydroxy tin oxide as catalysts were added to the resulting mixture. The reaction mixture was placed in a reactor with a rectifying column and the reaction was started at 190° C., 79.9 kPa. The reaction was carried out for 270 minutes while raising the temperature stepwise to obtain an esterification reaction product. The density of the distillate obtained during the esterification reaction was measured to determine the THF content in the distillate, and the amount of the by-produced THF (g/kg PBT) was calculated according to the Equations 2 to 4. As Comparative Example 5, the esterification reaction was carried out in the same manner as described above for the 1,4-butanediol obtained by the same operations except that sodium hydroxide was not added. The results were shown in Table 6.

Example 9

Treatment with Nanofiltration Membrane and Purification by Distillation with Added Alkaline Substance of Model Fermentation Broth Containing 1,4-Butanediol, and Evaluation of Esterification Reaction of Obtained 1,4-Butanediol and Dicarboxylic Acid Treatment with Nanofiltration Membrane of Model Fermentation Broth Containing 1,4-Butanediol The model fermentation broth described in Table 5 was purified by the membrane separation apparatus shown in FIG. 1. As a nanofiltration membrane 2, a spiral type membrane element "SU-610" (commercially available from TORAY INDUSTRIES, INC.) was used. The above-described model fermentation broth containing 1,4-butanediol was fed to a feed tank 1, and the apparatus was driven at a feed water pressure of 2 MPa and a feed water temperature 18° C. to carry out the purification with a nanofiltration membrane.

Distillation of Aqueous 1,4-Butanediol Solution after Nanofiltration Treatment with Added Alkaline Substance The aqueous 1,4-butanediol solution after nanofiltration treatment was concentrated by a thin film concentrator MF-10 (commercially available from TOKYO RIKAKIKAI) at a reduced pressure of 30 hPa and at a raised temperature of 60° C. to obtain an aqueous 50 wt % 1,4-butanediol solution. To 200 g of the concentrated 1,4-butanediol solution, 0.75 g of sodium hydroxide (1.7 mol % based on the amount (number of moles) of 1,4-butanediol) was added and the resulting solution was well stirred until sodium hydroxide is dissolved. The resulting solution was subjected to distillation under reduced pressure (1.3 mmHg) at 130° C. to obtain purified 1,4-butanediol. The analytical results of the obtained 1,4-butanediol for the GC purity, degree of pigmentation (APHA) and total ion concentration are shown in Table 6.

Esterification Reaction Between Distilled 1,4-Butanediol and Dicarboxylic Acid

Using the 1,4-butanediol after the nanofiltration treatment followed by distillation with added alkaline substance, an esterification reaction was carried out in the same manner as in Example 8 to obtain esterification reaction product. The amount of by-produced THF (g/kg PBT) was calculated in the same manner as in Example 8. The results are shown in Table 6.

Example 10

Ion Exchange Treatment and Purification by Distillation with Added Alkaline Substance of Model Fermentation Broth Containing 1,4-Butanediol, and Evaluation of Esterification Reaction of Obtained 1,4-Butanediol and Dicarboxylic Acid Ion Exchange Treatment of Model Fermentation Broth Containing 1,4-Butanediol The model fermentation broth described in Table 5 was subjected to an ion exchange treatment to remove the residual ions. A strong cation exchange resin "IR410J" (commercially available from ORGANO) and a strong anion exchange resin "IR120" (commercially available from ORGANO) were used. These ion exchange resins were used after regeneration to OH type and H type, respectively, by treatments with 1N sodium hydroxide and 1N hydrochloric acid, respectively. The amounts of the resins were calculated such that the total amount of the various inorganic salts and organic acid salts was half of the ion exchange capacities of the resins, respectively. The respective above-described ion exchange resins were packed into columns, and the solution passed through the anion exchange column and then through cation exchange column at a flow rate SV=10.

Distillation of Aqueous 1,4-Butanediol Solution after Ion Exchange Treatment with Added Alkaline Substance The aqueous 1,4-butanediol solution after ion exchange treatment was concentrated and then distilled with added alkaline substance in the same manner as in Example 9 to obtain purified 1,4-butanediol. The analytical results of the obtained 1,4-butanediol for the GC purity, degree of pigmentation (APHA) and total ion concentration are shown in Table 6.

Esterification Reaction Between Distilled 1,4-Butanediol and Dicarboxylic Acid

Using the 1,4-butanediol after the ion exchange treatment followed by distillation with added alkaline substance, an esterification reaction was carried out in the same manner as in Example 8 to obtain esterification reaction product. The amount of by-produced THF (g/kg PBT) was calculated in the same manner as in Example 8. The results are shown in Table 6.

TABLE 6

|  |  | Comparative Example 5 | Example 8 | Example 9 | Example 10 |
|---|---|---|---|---|---|
|  | Nanofiltration membrane treatment | No | No | Yes | No |
|  | Ion exchange treatment | No | No | No | Yes |
|  | Amount of added alkaline substance [mol % based on 1,4-BDO] | — | 1.7 | 1.7 | 1.7 |
| Quality of 1,4-BDO after distillation | GC purity [%] | 92.3 | 98.2 | 98.5 | 99.9 |
|  | Degree of pigmentation | 101 | 66 | 38 | 6 |
|  | Total ion concentration [ppm] | 89 | 13 | 3 | 1 |
| Esterification | Completion of reaction | No | Yes | Yes | Yes |
|  | Amount of by-produced THF [g/kg PBT] | 99 | 61 | 51 | 61 |

As shown in Table 6, the qualities of 1,4-butanediol (the GC purity, degree of pigmentation and total ion concentration) are increased by carrying out nanofiltration treatment or ion exchange treatment before distillation with added alkaline substance. It was also shown that esterification reactions were completed when the distillation was carried out with alkaline substance. Additionally, the amount of by-produced THF (g/kg PBT) was notably decreased in when using 1,4-butanediol obtained by nanofiltration treatment followed by distillation with adding alkaline substance.

INDUSTRIAL APPLICABILITY

The 1,4-butanediol obtained by our processes has a high purity and coloration thereof is small. When a polyester is produced using as a material the 1,4-butanediol obtained by our processes, by-production of THF during the esterification reaction of 1,4-butanediol is reduced and the delay in the polymerization can be prevented.

What is claimed is:

1. A process of producing 1,4-butanediol, comprising the steps of
    (a) adding an alkaline substance other than an ammonia or an amine to an aqueous 1,4-butanediol-containing solution originated from a fermentation broth;
    (b) distilling the resulting mixture of step (a); and
    (c) recovering a 1,4-butanediol-containing solution from vapor flow,
    wherein, before adding said alkaline substance, said aqueous 1,4-butanediol-containing solution originated from a fermentation broth is subjected to a step of filtering said aqueous 1,4-butanediol-containing solution through a nanofiltration membrane and recovering the aqueous 1,4-butanediol-containing solution from the permeate flow of the membrane; and/or a step of subjecting said aqueous 1,4-butanediol-containing solution to an ion exchange treatment.

2. The process according to claim 1, wherein said alkaline substance is added in an amount of not more than 20 mol % based on the 1,4-butanediol.

3. The process according to claim 1, wherein said alkaline substance is at least one selected from the group consisting of alkaline metal hydroxides, alkaline metal salts, alkaline earth metal hydroxides and alkaline earth metal salts.

4. The process according to claim 1, wherein said alkaline substance is at least one selected from the group consisting of sodium hydroxide, potassium hydroxide, calcium hydroxide, magnesium hydroxide, sodium carbonate and calcium carbonate.

5. The process according to claim 1, wherein, before adding said alkaline substance, said aqueous 1,4-butanediol-containing solution originated from a fermentation broth is subjected to a step of filtering said aqueous 1,4-butanediol-containing solution through a reverse osmosis membrane to increase the concentration of 1,4-butanediol.

6. A process of producing a polyester comprising reacting the 1,4-butanediol produced by the process according to claim 1 with a dicarboxylic acid.

7. The process according to claim 6, wherein said dicarboxylic acid is terephthalic acid.

8. The process according to claim 2, wherein said alkaline substance is at least one selected from the group consisting of alkaline metal hydroxides, alkaline metal salts, alkaline earth metal hydroxides and alkaline earth metal salts.

9. The process according to claim 2, wherein said alkaline substance is at least one selected from the group consisting of sodium hydroxide, potassium hydroxide, calcium hydroxide, magnesium hydroxide, sodium carbonate and calcium carbonate.

10. The process according to claim 3, wherein said alkaline substance is at least one selected from the group consisting of sodium hydroxide, potassium hydroxide, calcium hydroxide, magnesium hydroxide, sodium carbonate and calcium carbonate.

11. The process according to claim 2, wherein, before adding said alkaline substance, said aqueous 1,4-butanediol-containing solution originated from a fermentation broth is subjected to a step of filtering said aqueous 1,4-butanediol-containing solution through a reverse osmosis membrane to increase the concentration of 1,4-butanediol.

12. The process according to claim 3, wherein, before adding said alkaline substance, said aqueous 1,4-butanediol-containing solution originated from a fermentation broth is subjected to a step of filtering said aqueous 1,4-butanediol-containing solution through a reverse osmosis membrane to increase the concentration of 1,4-butanediol.

13. The process according to claim 4, wherein, before adding said alkaline substance, said aqueous 1,4-butanediol-containing solution originated from a fermentation broth is subjected to a step of filtering said aqueous 1,4-butanediol-containing solution through a reverse osmosis membrane to increase the concentration of 1,4-butanediol.

14. A process of producing a polyester comprising reacting the 1,4-butanediol obtained by the process according to claim 2 with a dicarboxylic acid.

15. A process of producing a polyester comprising reacting the 1,4-butanediol obtained by the process according to claim 3 with a dicarboxylic acid.

* * * * *